United States Patent
Schweizer et al.

(10) Patent No.: US 11,311,267 B2
(45) Date of Patent: Apr. 26, 2022

(54) METHOD OF POSITION PLANNING FOR A RECORDING SYSTEM OF A MEDICAL IMAGING DEVICE AND MEDICAL IMAGING DEVICE

(71) Applicant: Siemens Healthcare GmbH, Erlangen (DE)

(72) Inventors: Hans Schweizer, Plattling (DE); Christian Scipio, Nuremberg (DE); Hermann Georg Mayer, Prien am Chiemsee (DE); Veronika Heinrich, Munich (DE)

(73) Assignee: Siemens Healthcare GmbH, Erlangen (DE)

( * ) Notice: Subject to any disclaimer, the term of this patent is extended or adjusted under 35 U.S.C. 154(b) by 70 days.

(21) Appl. No.: 16/966,449

(22) PCT Filed: Nov. 20, 2018

(86) PCT No.: PCT/EP2018/081864
§ 371 (c)(1),
(2) Date: Jul. 30, 2020

(87) PCT Pub. No.: WO2019/149400
PCT Pub. Date: Aug. 8, 2019

(65) Prior Publication Data
US 2021/0038181 A1 Feb. 11, 2021

(30) Foreign Application Priority Data
Jan. 31, 2018 (EP) .................................... 18154435

(51) Int. Cl.
*A61N 5/10* (2006.01)
*G06T 7/33* (2017.01)
(Continued)

(52) U.S. Cl.
CPC ............... *A61B 6/547* (2013.01); *A61B 6/06* (2013.01); *A61B 6/4405* (2013.01);
(Continued)

(58) Field of Classification Search
CPC ...... A61N 5/103; A61N 5/10069; G06T 7/37; G06T 7/13; G06T 7/337; G06T 7/70;
(Continued)

(56) References Cited

U.S. PATENT DOCUMENTS

2013/0336445 A1   12/2013  Sehnert
2017/0224298 A1    8/2017  Hannemann
(Continued)

FOREIGN PATENT DOCUMENTS

DE    102010062090 A1    5/2012
DE    102012205238 A1   10/2013
(Continued)

OTHER PUBLICATIONS

International Search Report and the Written Opinion for International Patent Application PCT/EP2018/081864 dated Mar. 6, 2019.
(Continued)

*Primary Examiner* — Don K Wong
(74) *Attorney, Agent, or Firm* — Lempia Summerfield Katz LLC (57) ABSTRACT

A method of position planning for a recording system of an imaging device with respect to a selectable field of view of a patient includes acquiring current position information of the recording system and/or the imaging device, and/or setting information of a collimator of the imaging device. A current intersection volume between an X-ray beam and the patient and/or a current field of view is determined. The current intersection volume and/or the current field of view is determined as a virtual display element. A target intersection volume and/or a target field of view is received by
(Continued)

manipulation of the virtual display element. A target position of the recording system and/or the imaging device, and/or the setting of the collimator is determined, such that, on occupying the target position, the target intersection volume and/or the target field of view becomes the current intersection volume and/or current field of view.

17 Claims, 4 Drawing Sheets

(51) Int. Cl.
*A61B 6/00* (2006.01)
*A61B 6/06* (2006.01)
*G06T 19/00* (2011.01)

(52) U.S. Cl.
CPC ............ *A61B 6/4441* (2013.01); *A61B 6/466* (2013.01); *A61B 6/469* (2013.01); *G06T 19/006* (2013.01); *G06T 2219/2004* (2013.01)

(58) Field of Classification Search
CPC . G06T 2207/30204; G06T 2207/10048; G06T 2207/10072
See application file for complete search history.

(56) References Cited

U.S. PATENT DOCUMENTS

2018/0228556 A1   8/2018   Schweizer
2019/0111279 A1*  4/2019   Berlinger ................. G06T 7/37

FOREIGN PATENT DOCUMENTS

DE   102012215496 A1   3/2014
DE   102014216718 A1   2/2016

OTHER PUBLICATIONS

Schweizer et al, Input method for movement control of mobile X-ray devices; Feb. 24, 2017. pp. 1-8.

* cited by examiner

METHOD OF POSITION PLANNING FOR A RECORDING SYSTEM OF A MEDICAL IMAGING DEVICE AND MEDICAL IMAGING DEVICE

This application is the National Stage of International Application No. PCT/EP2018/081864, filed Nov. 20, 2018, which claims the benefit of European Patent Application No. EP 18154435.4, filed Jan. 31, 2018. The entire contents of these documents are hereby incorporated herein by reference.

BACKGROUND

The present embodiments relate to position planning for a recording system of a medical imaging device.

Imaging medical devices (e.g., permanently installed radiography systems or mobile C-arm devices) nowadays typically use the following techniques to preview the region of the body of the patient to be recorded. For example, the 2D field of view may be displayed by projection directly onto the patient. This is usually achieved by a plurality of line lasers or the projection of a light "window" directly onto the surface of the patient. The projection hardware is installed in the imaging device for this purpose (e.g., on the image recorder and/or emitter housing). As another example, a virtual preview of the field of view is provided on the monitor of the imaging system via a polygonal line (e.g., a rectangle).

These methods are not very flexible, however, and require the user to manually adjust the position of the imaging system until the desired target region for recording is reached. Using the methods from technique 2, this may be improved to some extent but, for example, in the setup of 3D scans, the 2D projections onto the surface of the patient may provide only an incomplete impression of the resulting reconstruction volume or a corresponding position relative to the patient. This is sometimes a problem, for example, with mobile C-arms with a spatially very limited reconstruction volume (e.g., cube with approximately 16 cm edge length in the case of Cios Spin) if relatively large target structures are to be depicted by a scan. The optimum positioning of the volume in order to acquire all structures simultaneously requires quite a bit of experience on the part of the OP team to position the C-arm optimally for the recording or the 3D scan.

SUMMARY AND DESCRIPTION

The scope of the present invention is defined solely by the appended claims and is not affected to any degree by the statements within this summary.

The present embodiments may obviate one or more of the drawbacks or limitations in the related art. For example, a method that overcomes the drawbacks from the prior art is provided. As another example, an imaging device suitable for carrying out the method is provided.

A method of one or more of the present embodiments of position planning for a recording system of an imaging device with respect to a selectable field of view of a patient includes acquiring or receiving current position information of the recording system and/or the imaging device and/or setting information of a collimator of the imaging device. Current position information of the patient is acquired or received, and a current course of an X-ray beam that may be emitted by the recording system is determined. A current intersection volume between the X-ray beam and the patient (e.g., a patient covering determined from the position information of the patient) and/or a current field of view is determined from the current course of the X-ray beam and a patient covering. The current intersection volume and/or the current field of view is determined as a virtual display element. A target intersection volume and/or a target field of view is received by manipulation of the virtual display element. A target position of the recording system and/or the imaging device and/or the setting of the collimator is determined such that, on occupying the target position, the target intersection volume and/or the target field of view becomes the current intersection volume and/or current field of view.

A manipulation of the display element may, in this connection, be a change thereof (e.g., a displacement or twisting, change in position, size, orientation, etc.).

In one embodiment, the current position of the patient, or of parts of the patient, and the position (e.g., the contour) of the imaging system (e.g., the mobile C-arm device), recording system (e.g., only X-ray source and X-ray detector), or information relating to the collimator system is acquired by suitable, known position-determining methods (e.g., tracking methods) once, continuously, or in predefined intervals. This acquisition may be made, for example, by an external 3D tracking camera and suitable marker structures that are fastened to the patient and the imaging system (e.g., a C-arm) (e.g., outside-in tracking). In another embodiment, corresponding tracking HW, as is used in mixed reality or augmented reality (AR) glasses (e.g., MS HoloLens), may be used (e.g., inside-out tracking). A combination of the two methods is also possible in order to increase the robustness. In addition, other possibilities for acquiring the positions may be used too, or the positions may be received from existing data.

The acquired positions and data are forwarded, for example, to a control unit (e.g., a controller) of the imaging device. Consequently, the control unit knows the current position of the image system and patient relative to each other or may determine this. In one or more of the present embodiments, a current intersection volume between the X-ray beam and the patient (e.g., a patient covering determined from the position information of the patient) and/or a current field of view is determined from the current course of the X-ray beam and a patient covering. A virtual display element is displayed on a display unit (e.g., 2D screen or in stereoscopic form on the AR glasses). The display unit depicts the current intersection volume and/or the current field of view. This may also be cross-faded, for example, with the real patient. This display element depicts (e.g., in the case of a planned 2D recording) the intersection between patient volume and collimated direct radiation course of the X-ray radiation. According to one embodiment, the virtual display element may be manipulated by an operator using at least one operating element and/or input unit. The user may manipulate the display element on the display unit (e.g., 2D screen), for example, using a suitable graphic user interface (GUI) operating elements (e.g., graphic drag points, sliders, or the like) and a known input device (e.g., mouse and keyboard, touchscreen, or the like). According to one embodiment, the virtual display element is displaceable and/or changeable with respect to size, position, and orientation. If AR glasses are used for the display, the field of view may be manipulated, for example, also by gesture control in that the user manipulates the holographically overlaid volume directly on the patient. In addition to gesture control, the position, acceleration, and magnetic field sensors of conventional glasses may also be included in the interaction in order, for example, to influence the orientation of the system by head movements.

In one or more of the present embodiments, a target intersection volume and/or a target field of view is received by the system by a manipulation of the virtual display element. A target position of the recording system and/or the imaging device and/or the setting of the collimator is then determined herefrom such that, on occupying the target position, the target intersection volume and/or the target field of view becomes the current intersection volume and/or current field of view.

For this, movement commands for the different device axes (e.g., position of the C-arm relative to the patient, orbital/angular angle, height of the vertical axis) and/or the settings of the collimator may be derived, for example, by the control unit on confirmation of the target intersection volume and/or target field of view. The calculation of the device movements may include, for example, collision sensor parameters too in order to automatically determine and optionally dynamically adjust the optimum movement sequence in relation to device positioning.

Instead of 2D recordings, 3D scans may also be provided. For this, instead of the intersection of direct radiation and the patient volume, for example, the 3D reconstruction volume (e.g., a cube) technically possible with the imaging device is superimposed (e.g., in the original size) on the patient or the patient covering. The user may then manipulate the position of the volume as described.

A further embodiment of a method of position planning for a recording system of an imaging device with respect to a selectable field of view of a patient includes: acquiring or receiving current position information of the recording system and/or the imaging device and/or setting information of a collimator of the imaging device; acquiring or receiving current position information of the patient; determining a current 3D reconstruction volume that may be recorded by the recording system during a current position; determining a current recording volume from the current 3D reconstruction volume and a patient covering; displaying the current recording volume as a virtual display element; receiving a target intersection volume by manipulation of the virtual display element; and determining a target position of the recording system and/or the imaging device and/or the setting of the collimator such that, on occupying the target position, the target recording volume becomes the current recording volume.

The recording system and/or the imaging device and/or the setting of the collimator may be moved into the target position.

According to one embodiment, the recording system is formed by a C-arm, and/or the imaging device is formed by a mobile C-arm device. Mobile C-arm devices have C-arms that are fastened to a device trolley and may be moved in a variety of ways (e.g., may be rotated and translated). The device trolley may also be automatically or manually freely moved. Permanently installed C-arm devices also have moveable C-arms. Therefore, for example, a C-arm may be arranged on an articulated robot and adjusted in any desired spatial directions.

According to a further embodiment, the current intersection volume or the current field of view or the current recording volume and the current patient covering are displayed together (e.g., on the corresponding display unit). The display unit may be formed by a monitor or a smart device or a virtual or augmented reality display unit (e.g., augmented reality glasses).

According to a further embodiment, the current position information of the recording system and/or the imaging device and/or the setting information of a collimator of the imaging device and/or the current position information of the patient is regularly or continuously updated. Reliable functioning of the method may be provided in this way.

According to a further embodiment, a sequence of a plurality of target intersection volumes or target fields of view or target recording volumes are received, and corresponding target positions are determined and occupied. The corresponding recordings may then be performed in each of the target positions. A sequence of recordings of this kind (e.g., panorama) may be provided if the target intersection volume and/or the target field of view exceeds the dimensions that may be depicted by a recording (e.g., ultimately limited by the size of the image recorder). The control unit may plan the sequence of recordings and/or the movement vectors corresponding to a necessary sequence over time.

If the normal reconstruction volume of a conventional individual scan (e.g., orbital scan with a C-arm) is not sufficient in terms of size, then a type of 3D panorama, from which required trajectories and movement patterns for the imaging system may be derived in the framework of the technically imposed restrictions of this method, may be calculated.

According to a further embodiment, a correctly positioned superimposition of previously made recordings of the patient is performed on a display unit. In this connection, for example, preoperatively created 2D recordings or 3D scans (e.g., CT or MRT) may be corrected in terms of position and/or may be superimposed on the patient in original size for the purpose of better orientation. This may be advantageous if, for example, particular regions are to be recorded again for control purposes in order, for example, to check the position of implants or to operate on a tumor. Size comparisons of relevant structures with respect to the change since the last recording are also made possible hereby. It may also be advantageous that the physician has already marked the position of relevant structures in a corresponding planning system before the procedure and a control unit then already determines (e.g., in the OP with knowledge of the patient position) the necessary recording positions of the imaging device (e.g., mobile C-arm) for intraoperative 2D recordings or 3D scans.

The method of one or more of the present embodiments simplifies clinical workflows in that the currently conventional, laborious positioning interaction with the imaging device (e.g., C-arm) is largely eliminated and replaced by a patient- or image-centered approach. The optimum device position is automatically determined in the process. Volume-capturing camera systems and optionally AR glasses, for example, are used as aids. The method serves as an intuitive, clear, and fast positioning aid for a user or an operator of a medical imaging device to simplify workflows and improve patient care.

The present embodiments also include a medical imaging device for carrying out a method. The medical imaging device includes a recording system with an X-ray detector and an X-ray source, a collimator for collimating an X-ray beam that may be emitted by the X-ray source, and a control device (e.g., a controller) for controlling the method. The medical imaging device also includes a calculating unit for determining the current intersection volume or the current field of view or the current recording volume, a display unit for displaying the current intersection volume, the current field of view, or the current recording volume as a virtual display element, and an input unit (e.g., an input) for manipulation of the display element.

According to one embodiment, the device also includes a tracking system for acquiring current position information of the recording system and/or the imaging device and/or setting information of a collimator, and for acquiring current position information of the patient. A tracking system of this kind may be formed, for example, by a 3D camera (e.g., an external camera) or augmented reality glasses. An external 3D tracking camera may also rely on, for example, suitable marker structures that are fastened, for example, to the patient and the recording system (e.g., a C-arm) (e.g., outside-in tracking). It is also possible to use corresponding tracking hardware as is used in mixed reality or augmented reality (AR) glasses (e.g., MS HoloLens) (e.g., inside-out tracking). A combination of the two methods is also possible to increase the robustness.

The present embodiments also include a method for depicting the field of view of a recording system of an imaging device. The method includes: acquiring current position information of the recording system and/or the imaging device and/or setting information of a collimator of the imaging device; acquiring current position information of a patient; determining a current course of an X-ray beam that may be emitted by the recording system; determining a current intersection volume between the X-ray beam and the patient (e.g., a patient covering determined from the position information of the patient) and/or a current field of view from the current course of the X-ray beam and a patient covering; and displaying the current intersection volume and/or current field of view.

DETAILED DESCRIPTION

Figure 1:
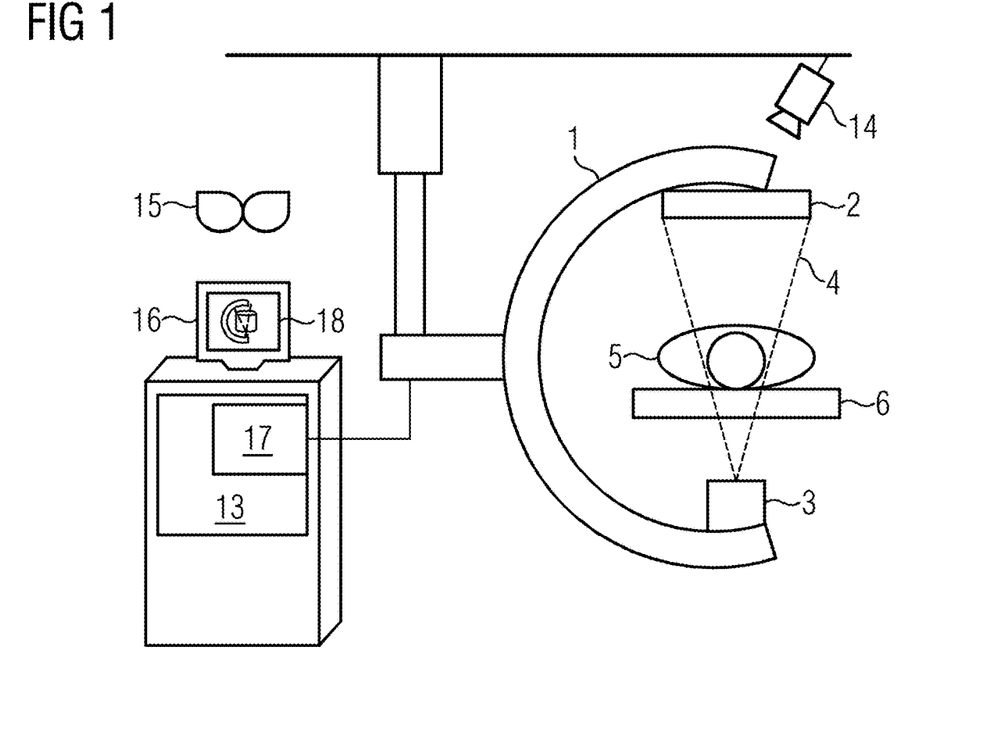
FIG. 1 shows one embodiment of an imaging device with a recording system and a display unit.

FIG. 1 shows one embodiment of a medical imaging device with a C-arm 1, to which an X-ray detector 2 and an X-ray source 3 are fastened. The X-ray source 3 may emit an X-ray beam 4 additionally shaped or shapeable by a collimator (not shown). The X-ray beam 4 penetrates a patient 5 supported on a patient couch 6. A position and/or a covering of the C-arm and a position of the patient 5 (e.g., in the form of a patient covering) are acquired, for example, by an acquisition system (e.g., a tracking system with a three-dimensional (3D) tracking camera 14). The recording system (e.g., the C-arm 1 with the X-ray source 3 and the X-ray detector 2) may be moved with respect to the patient 5 (e.g., may be rotated and translated). The recording system may be fastened, for example, by a bracket to the ceiling, the floor, or a device trolley. The imaging device is controlled by a system controller 13 that controls emission of the X-ray radiation and movements of the recording system (e.g., when instructed or automatically). In addition, the imaging device also has a calculating unit 17 (e.g., a calculator) and an operating unit with a display unit (e.g., a touch monitor 16 with a display 18). The imaging device may be used for carrying out a method of the present embodiments.

Figure 5:
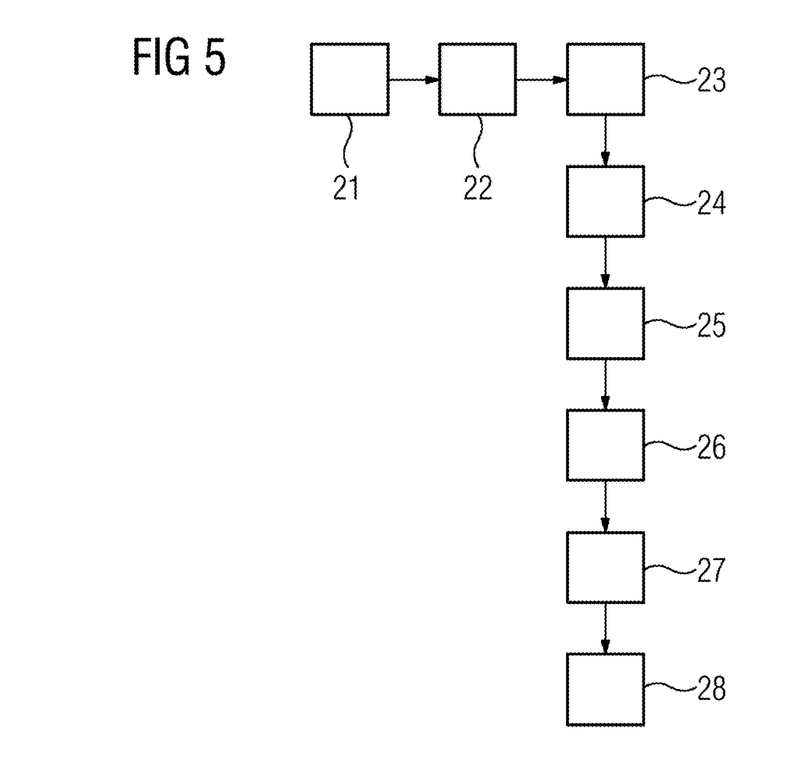
FIG. 5 shows a sequence of one embodiment of a method.

FIG. 5 shows a progression of one embodiment of a method. In act 21, current position information of the recording system and/or the imaging device and/or setting information of a collimator of the imaging device is acquired or received (e.g., by an acquisition system). An acquisition system of this kind may be formed, for example, by the tracking system with 3D-tracking camera 14. For this, if required, suitable marker structures, which are fastened to the patient and the imaging system (e.g., a C-arm) are also used (e.g., outside-in tracking). In one embodiment, corresponding tracking hardware as is used in mixed reality or augmented reality (AR) glasses (e.g., MS HoloLens) may be used (e.g., inside-out tracking). FIG. 1 shows, by way of example, in this regard, augmented reality glasses 15. In addition, other possibilities may be used for acquiring the positions, or the positions may be received from existing data (e.g., previously taken X-ray image).

In act 22, current position information of the patient 5 or of parts/organs of the patient 5 are acquired or received. This may also be acquired by the tracking system. A patient covering or organ covering, for example, may be determined from the position information. In a third act 23, a current course of an X-ray beam that may be emitted by the recording system is determined. For example, the position information of the entire imaging device or of only the recording system and/or information of the collimator is/are used to determine, for example, the current course of the X-ray beam 4. No actual X-ray radiation has to be emitted for this; instead, just the planned or intended settings (e.g., of the collimator) may be used as well.

In act 24, a current intersection volume between the X-ray beam 4 and the patient 5/the patient covering, and/or a current field of view or a current recording volume is determined from the current course of the X-ray beam and the position of the patient/the patient covering. This may be carried out, for example, in that the acquired positions and data are forwarded to the control unit 13 of the imaging device. Consequently, the control unit knows the current position of the image system and patient/patient covering/organ covering relative to each other or may determine the current position.

Figure 2:
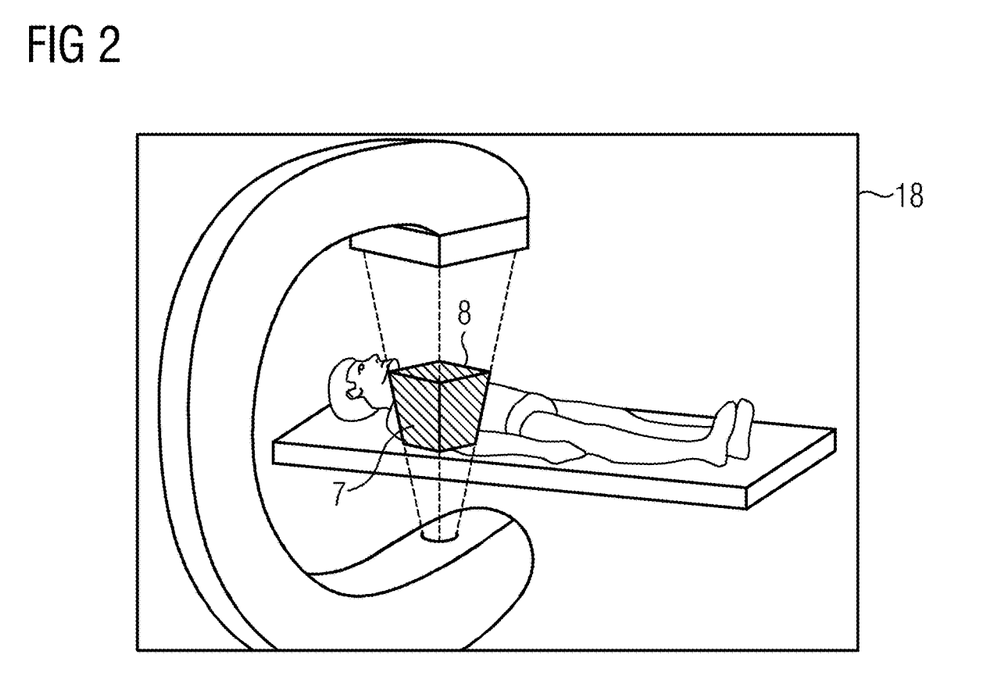
FIG. 2 shows an exemplary display of a current intersection volume of a patient covering and an X-ray beam and a virtual display element in the imaging device of FIG. 1.

In act 25, the current intersection volume 7 and/or the current field of view or current recording volume is/are displayed as a virtual display element 8 (illustrated in FIG. 2 and enlarged in FIG. 3) on, for example, a display 18 of a touch monitor 16. These may be jointly displayed with the current patient covering or the current patient position to give the user an exact representation of reality. Virtual display units may also be used in addition to real display units such as monitors, touchscreen, or tablets. The field of view is then easily produced from the current intersection volume 7 (e.g., with 2D recordings). In the 3D case, for example, a currently recordable recording volume may be determined by the technically possible 3D reconstruction volume, or the one possible in relation to the position of the imaging device, and the patient covering of the patient 5.

In act 26, a target intersection volume and/or a target field of view or a target recording volume is/are received by manipulation of the virtual display element (e.g., from a user input of an operator at the touch monitor). As shown in FIG.

Figure 4:
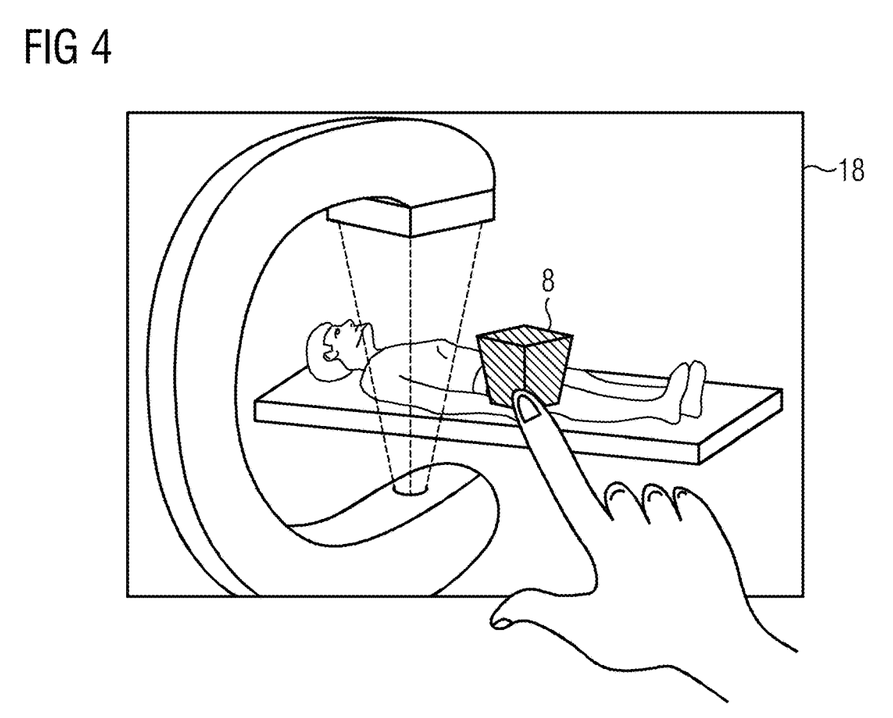
FIG. 4 shows a view of a manual displacement of the virtual display element of FIGS. 2 and 3.

4, the user/operator may displace the virtual display element 8; as an alternative, the user/operator may also change a position or orientation of the virtual display element 8 or manipulate the virtual display element 8 in some other way. This may be carried out, for example, by manual displacement of the virtual display element 8, as indicated in FIG. 4, using a hand. This may also be performed by clicking a mouse or another user input. Gesture control or acoustic control may also be used, for example. If AR glasses are used for display, the field of view may be manipulated (e.g., also by gesture control) in that the user manipulates the holographically superimposed volume directly on the patient. In addition to gesture control, the position, acceleration, and magnetic field sensors of conventional glasses may also be included in the interaction in order to influence, for example, the orientation of the system by head movements. As a result of the manipulation, the current intersection volume becomes the target intersection volume, the current field of view becomes the target field of view, or the current recording volume becomes the target recording volume.

In act 27, a target position of the recording system and/or the imaging device and/or the setting of the collimator is/are received such that, on occupying the target position, the target intersection volume and/or target field of view become the current intersection volume and/or current field of view. The imaging device or the control unit 13 and/or the calculating unit 17 then calculates from the target intersection volume which position the C-arm and/or the entire imaging device and/or the collimator is to occupy to form the current intersection volume from the target intersection volume. The imaging device or the control unit 13 and/or the calculating unit 17 alternatively calculates, from the target field of view or target recording volume, which position the C-arm, and/or the entire imaging device, and/or the collimator are to occupy to form the current field of view from the target field of view or the current recording volume from the target recording volume. The C-arm and/or the imaging device and/or the collimator may then be moved (e.g., automatically) into the corresponding position and/or setting. For this, movement commands for the different device axes (e.g., position of the C-arm relative to the patient, orbital/angular angle, height of the vertical axis) and/or the settings of the collimator may be derived (e.g., by the control unit) on confirmation of the target intersection volume and/or target field of view. Collision sensor parameters, for example, may also be incorporated in the calculation of the device movements to determine the optimum movement sequence for device positioning automatically and to optionally adjust the device movements dynamically.

In act 28, the target position of the recording system and/or the imaging device and/or the setting of the collimator is approached.

Figure 3:
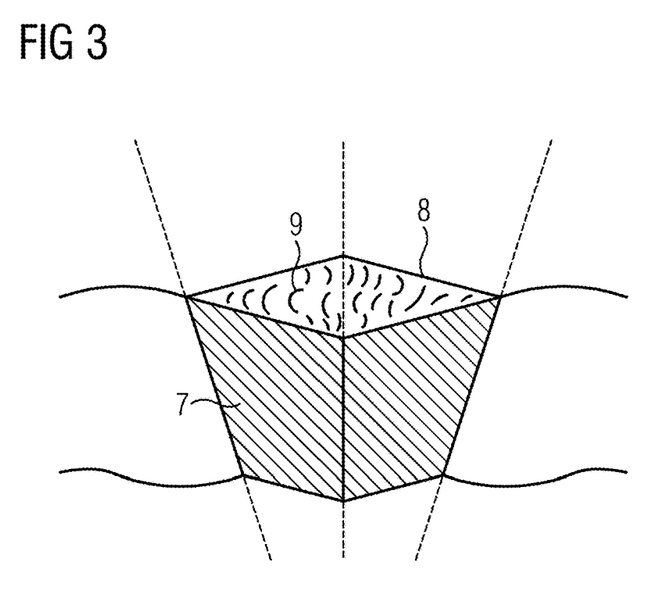
FIG. 3 shows an enlarged view of FIG. 2 with a superimposed two-dimensional (2D) recording.

FIG. 3 also shows in an enlarged detail that a previously recorded two-dimensional (2D) recording 9 of the patient 5 is superimposed in the region of the current intersection volume or field of view. This may be used by the user or the operator, for example, as an orientation or additional positioning aid.

The imaging device may be a permanently installed C-arm device or also, for example, a mobile C-arm device.

Figure 6:
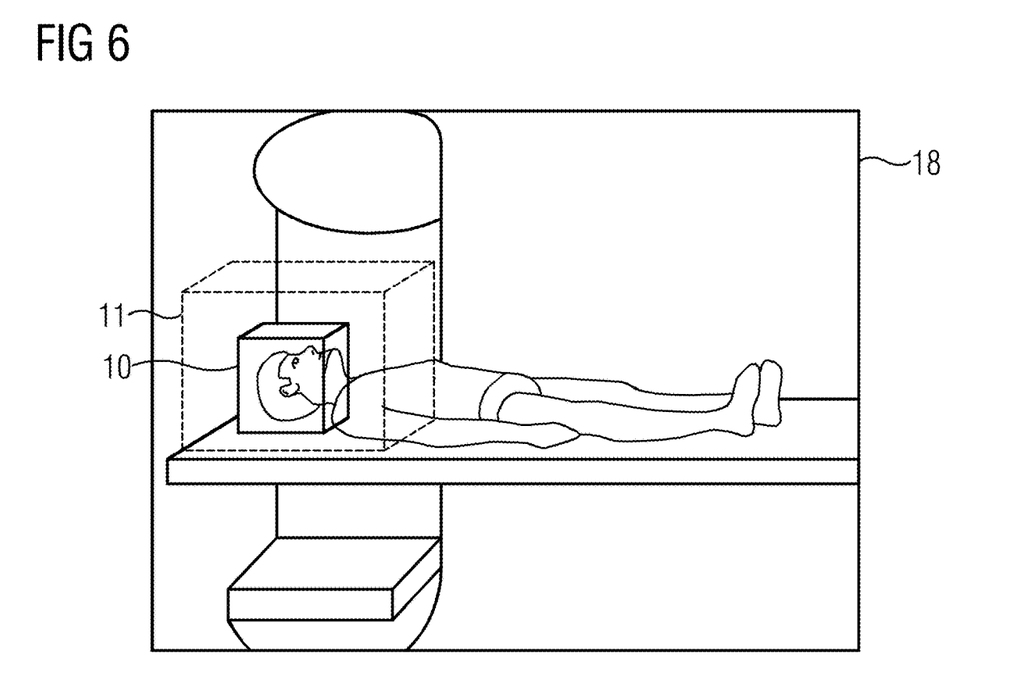
FIG. 6 shows an exemplary display of a current recording volume and a virtual display element in an imaging device for three-dimensional (3D) recordings.

FIG. 6 shows a currently recordable recording volume 10 for the case where 3D recordings are to be planned. In this case, the currently recordable recording volume 10 is determined by the technically possible 3D reconstruction volume 11, or the one possible 3D reconstruction volume 11 in relation to the position of the imaging device, and the patient covering of the patient 5. The imaging device (e.g., the C-arm 1) and the patient 5 are tracked as in the two-dimensional case by an acquisition system (e.g., tracking system).

Figure 7:
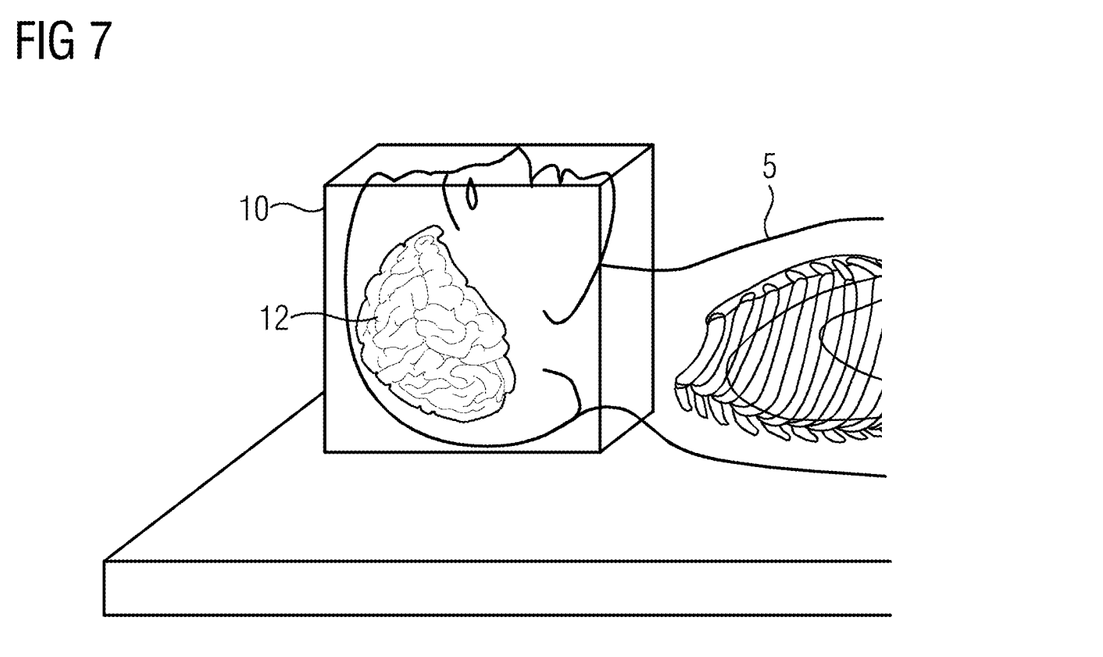
FIG. 7 shows an enlarged view according to FIG. 3 with a superimposed 3D recording.

FIG. 7 shows in a detail enlarged in relation to FIG. 6, how, in addition, a 3D volume image recorded previously (e.g., by angiography or CT) is overlaid with the current recording volume.

The current position information of the recording system and/or the imaging device and/or the setting information of a collimator of the imaging device and/or the current position information of the patient may be determined once or may also be regularly or continuously updated. Reliable functioning of the method may be provided in this way.

A sequence of a plurality of target intersection volumes or target fields of view or target recording volumes may also be received, and corresponding target positions may be determined and occupied. The corresponding scans may then be performed in each of the target positions. A sequence of recordings of this kind (e.g., panorama) may be provided if the target intersection volume and/or target field of view exceed(s) the dimensions that may be depicted by a recording (e.g., limited by the size of the X-ray detector). The control unit may plan the sequence of recordings and/or calculate the movement vectors corresponding to the required sequence over time.

The elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent. Such new combinations are to be understood as forming a part of the present specification.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A method of position planning for a recording system of an imaging device with respect to a selectable field of view of a patient, the method comprising:
   acquiring or receiving current position information of the recording system, the imaging device, or the recording system and the imaging device, setting information of a collimator of the imaging device, or a combination thereof;
   acquiring or receiving current position information of the patient;
   determining a current course of an X-ray beam that is emittable by the recording system;
   determining a current intersection volume between the X-ray beam and the patient, a current field of view, or the current intersection volume and the current field of view from the current course of the X-ray beam and a patient covering;
   displaying the current intersection volume, the current field of view, or the current intersection volume and the current field of view as a virtual display element;

receiving a target intersection volume, a target field of view, or the target intersection volume and the target field of view by manipulation of the virtual display element; and determining a target position of the recording system, the imaging device, or the recording system and the imaging device, the setting of the collimator, or a combination thereof such that, on occupying the target position, the target intersection volume and the target field of view, or the target intersection volume and the target field of view become the current intersection volume and the current field of view, or the current intersection volume and the current field of view.

2. A method of position planning for a recording system of an imaging device with respect to a selectable field of view of a patient, the method comprising:

acquiring or receiving current position information of the recording system, the imaging device, or the recording system and the imaging device, setting information of a collimator of the imaging device, or a combination thereof;

acquiring or receiving current position information of the patient;

determining a current three-dimensional (3D) reconstruction volume that is recordable by the recording system during a current position;

determining a current recording volume from the current 3D reconstruction volume and a patient covering;

displaying the current recording volume as a virtual display element;

receiving a target recording volume by manipulation of the virtual display element; and determining a target position of the recording system, the imaging device, or the recording system and the imaging device, a setting of the collimator, or a combination thereof such that, on occupying the target position, the target recording volume becomes the current recording volume.

3. The method of claim 1, wherein the recording system, the imaging device, the setting of the collimator, or any combination thereof is moved into the target position.

4. The method of claim 1, wherein the recording system is formed by a C-arm, the imaging device is formed by a mobile C-arm device, or a combination thereof.

5. The method of claim 1, wherein the field of view is two-dimensional or three-dimensional.

6. The method of claim 1, wherein the current intersection volume the current field of view, or the current recording volume, and the current patient covering or patient position are displayed together on a display unit.

7. The method of claim 6, wherein the display unit is formed by a monitor, a smart device, a virtual display element, or an augmented reality display unit.

8. The method of claim 1, wherein the virtual display element is displaceable, is configured to be changeable with respect to size, position, and orientation, or a combination thereof.

9. The method of claim 8, wherein the virtual display element is manipulatable by an operator using at least one operating element, input unit, or operating element and input unit.

10. The method of claim 1, wherein the current position information of the recording system, the imaging device, or the recording system and the imaging device, the setting information of the collimator of the imaging device, the current position information of the patient, or any combination thereof is regularly or continuously updated.

11. The method of claim 1, wherein a sequence of a plurality of target intersection volumes, target fields of view, or target recording volumes is received, and corresponding target positions are determined and occupied.

12. The method of claim 1, wherein a correctly positioned superimposition of previously taken recordings of the patient is performed on a display unit.

13. A medical imaging device comprising:
a recording system including an X-ray detector and an X-ray source;
a collimator operable to collimate an X-ray beam that is emittable by the X-ray source;
a controller configured to:
acquire or receive current position information of the recording system, an imaging device, or the recording system and the imaging device, setting information of the collimator, or a combination thereof;
acquire or receive current position information of a patient;
a calculator configured to:
determine a current course of an X-ray beam that is emittable by the recording system;
determine a current intersection volume between the X-ray beam and the patient, a current field of view, or a current recording volume;
a display operable to display the current intersection volume, the current field of view, or the current recording volume as a virtual display element; and
an input configured to manipulate the virtual display element,
wherein the controller is further configured to receive a target intersection volume, a target field of view, or the target intersection volume and the target field of view by manipulation of the virtual display element, and
wherein the calculator is further configured to determining a target position of the recording system, the imaging device, or the recording system and the imaging device, the setting of the collimator, or a combination thereof such that, on occupation of the target position, the target intersection volume and the target field of view, or the target intersection volume and the target field of view become the current intersection volume and the current field of view, or the current intersection volume and the current field of view.

14. The medical imaging device of claim 13, further comprising a tracking system operable to:
acquire the current position information of the recording system, the imaging device, or the recording system and the imaging device, the setting information of the collimator, or a combination thereof; and
acquire the current position information of the patient.

15. The medical imaging device of claim 14, wherein the tracking system is formed by a 3D-camera or augmented reality glasses.

16. The medical imaging device of claim 13, wherein the medical imaging device is formed by a mobile C-arm device.

17. The method of claim 1, wherein determining the current intersection volume between the X-ray beam and the patient, the current field of view, or the current intersection volume and the current field of view comprises determining the current intersection volume between the X-ray beam and the patient, and
wherein determining the current intersection volume between the X-ray beam and the patient comprises determining a current intersection volume between the X-ray beam and a patient covering determined from the position information of the patient.

* * * * *